United States Patent
Wagner

[11] Patent Number: 5,957,689
[45] Date of Patent: Sep. 28, 1999

[54] METHOD FOR INSTALLING A THROAT INSERT

[76] Inventor: John W. Wagner, 7701 Lakemont Dr. Northeast, Seattle, Wash. 98115-5234

[21] Appl. No.: 08/954,703

[22] Filed: Oct. 20, 1997

[51] Int. Cl.$^6$ ....................................................... A61C 5/00
[52] U.S. Cl. ............................ 433/215; 128/861; 128/862
[58] Field of Search .................................. 128/861, 862; 433/6, 37, 48, 215

[56] References Cited

U.S. PATENT DOCUMENTS

| | | | |
|---|---|---|---|
| 3,224,441 | 12/1965 | Monaghan | 128/862 |
| 3,303,844 | 2/1967 | Johnson et al. | 128/862 |
| 3,379,193 | 4/1968 | Monaghan | 128/862 |
| 3,407,808 | 10/1968 | Baldwin | 128/862 |
| 3,411,501 | 11/1968 | Greenberg | 128/862 |
| 4,495,945 | 1/1985 | Liegner | 128/862 X |
| 4,848,365 | 7/1989 | Guarlotti et al. | 128/862 X |
| 4,920,984 | 5/1990 | Furumichi et al. | 128/862 X |
| 5,277,203 | 1/1994 | Hays | 128/862 X |
| 5,566,684 | 10/1996 | Wagner | 128/862 X |
| 5,592,951 | 1/1997 | Castagnaro et al. | 128/862 X |

*Primary Examiner*—Nicholas D. Lucchesi
*Attorney, Agent, or Firm*—Robert W. Beach

[57] ABSTRACT

A flat blank of circular segmental shape having a recessed chord and made of thermoplastic material is heated in a bath of hot water in the range of 145 degrees F. (63 degrees C.) and 160 degrees F. (71 degrees C.) to render the material soft and supple. The blank is then manipulated and pressed in applying it to a dental arch for forming a facing alongside the oral cavity into which a throat insert is to be inserted for protecting the teeth of the arch from being injured, such as by being cracked or chipped, by impact with the teeth of such a throat insert or its appendages.

1 Claim, 2 Drawing Sheets

METHOD FOR INSTALLING A THROAT INSERT

BACKGROUND OF THE INVENTION

1. Field of the Invention

This invention relates to a protective facing for a dental arch and a method for making and using such facing by applying it to a dental arch.

2. Problem

The physiology of a human throat from the mouth and nose to the stomach and lungs includes, in descending order:

the pharynx, which is the cavity of the alimentary canal leading from the mouth and nasal passages to the larynx and esophagus;

airway to the lungs;

larynx, the cavity at the upper end of the trachea;

trachea, the tube extending from the larynx to its division into the two bronchi and forming the windpipe;

the bronchi or bronchial tubes branch to the left and right lungs to complete the wind pipe;

the esophagus, which is the passage for food from the pharynx to the stomach as distinguished from the airway.

Various types of medical apparatus are inserted into the foregoing passages of the throat for diagnostic exploration or treatment, such as the removal of a foreign object from a passage or the administration of anesthetic. Such medical devices include the:

pharyngoscope, which is an instrument for examining the pharynx;

laryngoscope, which is an instrument for examining the interior of the larynx;

endotracheal tube, which is a device for administering anesthetic gases or for examination;

bronchoscope, which is a slender tubular instrument with a small electric light for examining or treating the inside of the windpipe or the bronchi or for removing foreign bodies from them. All of these medical instruments are inserted through the oral cavity into a throat passage such as those defined above, so that such medical instruments will be referred to generically as throat inserts.

The passages through the throat are small, and a problem is to construct such a throat insert so that it will be small enough to be inserted into the throat without the use of excessive force.

The throat cavity is muscular and membranous, and its structure tends to reject an obstruction upward or to draw the obstruction downward into the stomach. Consequently, it is a further problem to anchor a throat insert so that its lower end can be maintained in a desired position for examination of a throat passage or for administration of an anesthetic. Anchoring appendages for an insert may be bulky and cumbersome and usually will be attached in some way to the patient's mouth.

Throat inserts and their appendages are usually made of hard material, such as metal or hard plastic, and, since it is necessary to apply considerable force to an insert for inserting it into a throat passage, and such an insert may buckle in the mouth during such insertion, it is not uncommon for a hard portion of throat insert apparatus to engage or strike one or more teeth sharply, particularly one or more teeth in the upper dental arch, which may crack or chip one or more teeth.

The purpose of the present invention is to prevent such injury to the patient's teeth.

SUMMARY OF THE INVENTION

A principal object of the present invention is to provide protection for teeth of a patient against damage by insertion of a throat insert through the patient's oral cavity into the patient's throat.

More specifically, it is an object to shield the patient's teeth with a facing or liner which will prevent injury to the teeth even if the facing is struck sharply by a throat insert or its appendages during installation of such throat insert and appendages.

The foregoing objects can be accomplished by applying a thin but tough and hard facing contiguously to the teeth of one or both of the patient's dental arches. Such application can be effected by providing a flat thin facing blank of thermoplastic material in the form of a sheet of appropriate size and shape which can be softened by being immersed briefly in fairly hot water. The softened facing blank is then pressed manually onto the dental arch to cover it contiguously. Cooling of the thermoplastic facing will result in it being hardened to provide an effective shield for the teeth protecting them from impacts or pressure against the facing effected by a throat insert or its appendages.

Prior Art

Mouthpieces fitted to a dental arch have previously been provided to be worn by a boxer or football player to protect the teeth, but these devices have been used in situations where the upper and lower and jaws are held clenched together by the wearer, whereas the facing of the present invention does not interfere with the insertion of a throat insert through the oral cavity, nor does it interfere with the application to the mouth of anchoring appendages for holding a throat insert in a desired location.

In addition, thermoplastic material which is suitable for the liner of the present invention has heretofore been used for dental purposes, such as disclosed in U.S. Pat. No. 4,401,616, issued Aug. 30, 1983, for Method of Making Custom Dental Impression Trays, and U.S. Pat. No. 4,776, 792, issued Oct. 11, 1988, for Dental Arch Occlusal Surface Print Recording Palate and Process of Using the Same. While the material used for making the articles disclosed in these patents can be satisfactorily used as the material from which the blank for the facing of the present invention is made, the types of articles for which such plastic material has previously been used are different from the liner blank of the present invention and serves a different purpose.

DETAILED DESCRIPTION

Throat inserts can be of various types, including pharyngoscopes, laryngoscopes, bronchoscopes and endotracheal tubes and their appendages for anchoring such throat inserts. The essence of the invention is to be able to shield easily and economically a dental arch alongside the oral cavity through which such a throat insert is inserted.

The present invention provides protection for the teeth of a dental arch by applying to the dental arch a hard tough facing or liner which will protect the teeth of the dental arch from being chipped or fractured by a throat insert or its appendages when being installed through the oral cavity adjacent to the dental arch. The facing is formed from a flat blank 1 of thermoplastic material shown in FIG. 1. The flat blank is of substantially uniform thickness of about one-sixteenth of an inch (1.6 mm) and is made of thermoplastic material which can be softened to be readily deformable by heating it for a short period of time, such as ten seconds, in a bath of water heated to a relatively hot temperature, such as between about 145 degrees F. (63 degrees C.) and about 160 degrees F. (71 degrees C.). When removed from the bath, the thermoplastic material will harden or set in a period of fifteen seconds to thirty seconds.

Thermoplastic material suitable for the blank 1 is manufactured by Rolyan Manufacturing Co., Inc. of Menomonee Falls, Wis., under its trademark "POLYFORM", as stated in U.S. Pat. No. 4,401,616, at column 4, lines 53 to 68. Advantages of such thermoplastic material are that, in unheated condition, it is hard but not brittle so that the blank 1 can be formed by diecutting or punching sheet material, or the material can be molded into the shape of the blank. When the blank is heated sufficiently, it becomes supple so that it can be easily bent, but it will not become sufficiently soft so that it will be stretched and thinned in places when pressure is applied to it. When heated as described, the blank is not too hot to be handled comfortably, so that it can be manipulated by manual pressure for applying it contiguously to the teeth of a dental arch.

Figure 1:
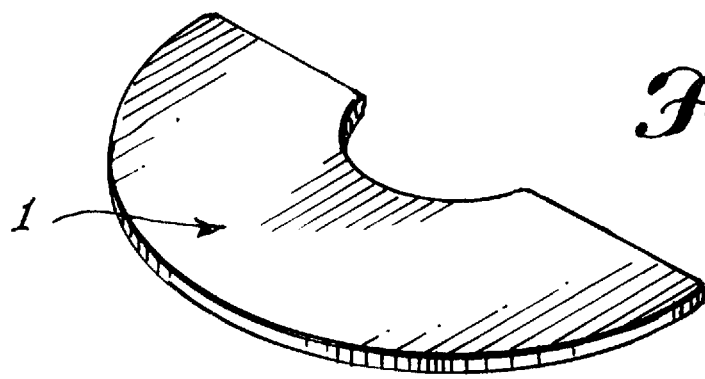
FIG. 1 is a top perspective of a blank for making the liner of the present invention.
Figure 2:
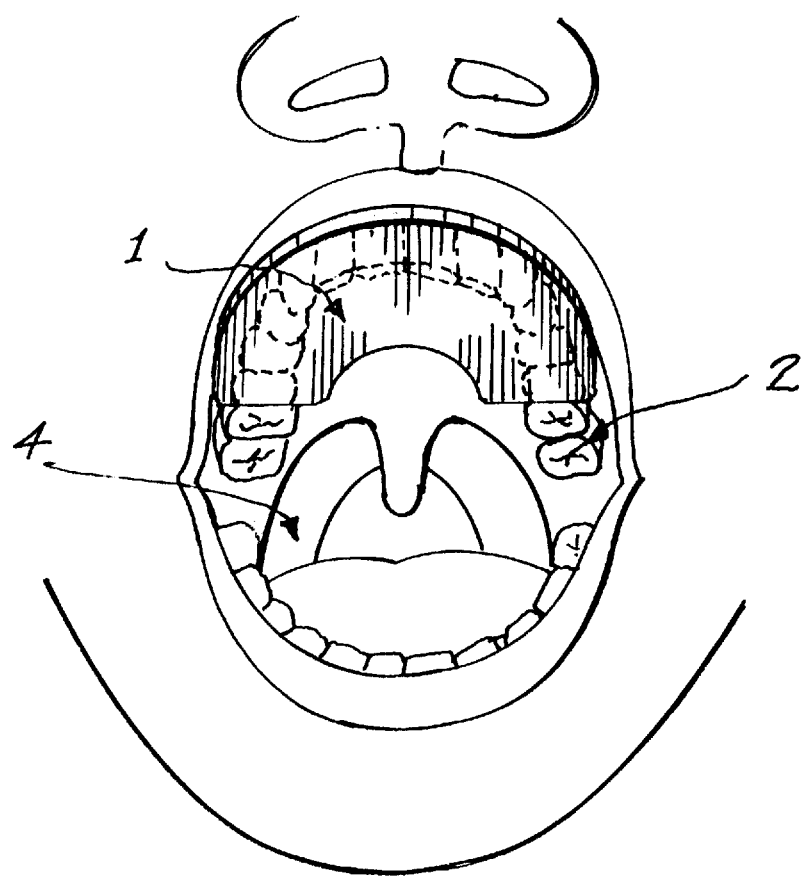
FIG. 2 is an exploded bottom perspective of an upper dental arch and a liner blank in a position preparatory to being formed by application to the dental arch.

As seen in FIG. 1, the blank 1 is of circular segmental shape having a recessed chord to more nearly approximate the shape of the dental arch 2 as shown in FIG. 2. To form the facing 3 shown in FIG. 3, it is only necessary to press the blank against the teeth of the dental arch and bend the edge portions of the blank into contact with the teeth. When thus formed, the facing 3 will revert to rigidity in a period of fifteen to thirty seconds without being subjected to artificial cooling. When thus set, the facing is hard but not brittle, so that it will not be cracked or shattered by being struck by a throat insert or its appendages.

Figure 3:
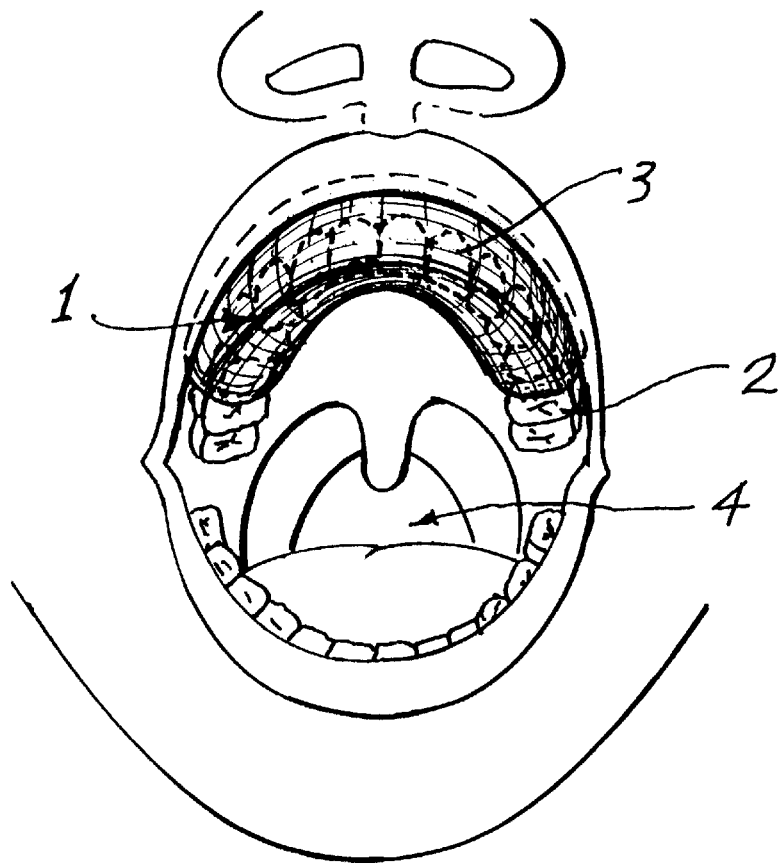
FIG. 3 is a bottom perspective showing the blank applied to an upper dental arch to form the liner.

As seen in FIG. 3, the liner 3 is located at one side of the oral cavity 4 through which a throat insert is inserted into a throat passage. The facing is compact, being of approximately one-sixteenth inch (1.6 mm.), in thickness so that it does not obstruct the oral cavity appreciably.

Figure 4:
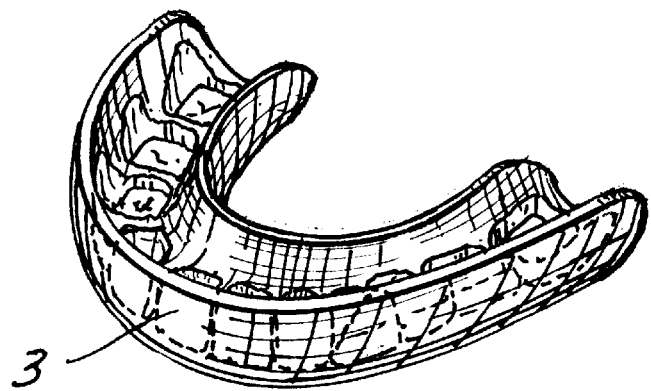
FIG. 4 is a top perspective of the formed liner after it has been removed from the upper dental arch.

During manipulation of a throat insert in the oral cavity, the liner 3 will adhere to the teeth of the dental arch sufficiently to maintain it in place applied to the dental arch without the provision of any special securing means or adhesive. Upon being softened by heat, however, the thermoplastic material is not made sticky, so that, after completion of the medical procedure, the liner can be removed readily from the dental arch by gentle traction to the condition shown in FIG. 4.

The shape of each dental arch is different for different individuals, so that a liner is used only once and is then discarded. The thermoplastic material of which the blank is made is economical, however, so that discarding of the liner is not appreciably wasteful.

I claim:

1. A method for installing a throat insert in a throat which comprises:

warming a flat thin substantially uniform thickness sheet blank of thermoplastic material to change such material from hard condition to soft supple condition;

placing the blank, which is of a size and shape to be received within the oral cavity, over a dental arch alongside the oral cavity;

pressing the blank manually onto and around the teeth of the dental arch and thereby deforming the blank into contiguous engagement with the teeth of the dental arch;

cooling the liner in place to body temperature to restore the hardness of the liner for providing a shield for the teeth of the dental arch alongside the oral cavity while leaving the oral cavity substantially unobstructed and leaving the jaws unimpaired to move open and closed;

inserting a throat insert past the liner formed in place on the dental arch into and through the oral cavity and into the throat while the liner remains in shielding position on the dental arch undisturbed by manipulation of the throat insert being inserted into and through the oral cavity; and removing the throat insert from the throat and out of the oral cavity while the dental arch remains shielded by the liner.

\* \* \* \* \*